United States Patent
Wilson

(10) Patent No.: US 9,522,084 B2
(45) Date of Patent: Dec. 20, 2016

(54) SLEEP SHIELD APPARATUS

(76) Inventor: Margarett A. Wilson, Atlanta, GA (US)

(*) Notice: Subject to any disclaimer, the term of this patent is extended or adjusted under 35 U.S.C. 154(b) by 1512 days.

(21) Appl. No.: 12/405,041

(22) Filed: Mar. 16, 2009

(65) Prior Publication Data

US 2010/0229275 A1    Sep. 16, 2010

(51) Int. Cl.
*A42B 3/18* (2006.01)
*A61F 9/04* (2006.01)
*A42B 1/18* (2006.01)
*A41D 13/11* (2006.01)

(52) U.S. Cl.
CPC .............. *A61F 9/04* (2013.01); *A41D 13/1184* (2013.01); *A61F 9/045* (2013.01)

(58) Field of Classification Search
CPC .... A41D 13/11; A41D 13/1184; A41D 23/00; A41D 13/1161; A41D 2300/32; A41D 20/00; A41D 2400/26; A42B 1/046; A42B 1/067; A42B 1/066; A42B 1/004; A42B 1/006; A42B 1/247; A42B 7/00; A47C 7/383
USPC ............. 2/9, 15, 171, 173, 174, 206, 209.3, 209.4, 2/452, DIG. 11; 128/857, 858; 5/636, 640
See application file for complete search history.

(56) References Cited

U.S. PATENT DOCUMENTS

| | | | |
|---|---|---|---|
| 766,963 A * | 8/1904 | Murray | 2/91 |
| 891,122 A * | 6/1908 | Wilcox | 2/206 |
| 1,761,664 A * | 6/1930 | Harris | 2/206 |
| 1,856,879 A * | 5/1932 | Lufkin | 2/205 |
| 2,119,439 A * | 5/1938 | Parmelee | 2/410 |
| 2,353,025 A * | 7/1944 | Gautreaux | 2/174 |
| 2,669,717 A * | 2/1954 | Diggs | 2/9 |
| 2,716,981 A * | 9/1955 | More | 604/303 |
| 2,874,385 A * | 2/1959 | Wade | 2/15 |
| 3,823,418 A * | 7/1974 | Piper | 2/206 |
| 4,259,748 A * | 4/1981 | Miller | 2/9 |
| 4,364,123 A * | 12/1982 | Sam | 2/9 |
| 4,589,408 A * | 5/1986 | Singer | 128/857 |
| 4,679,263 A * | 7/1987 | Honer | 5/640 |
| 4,786,159 A * | 11/1988 | Piazza et al. | 351/132 |
| 4,944,039 A * | 7/1990 | Dietrich | 2/13 |
| 4,969,473 A * | 11/1990 | Bothwell | 128/858 |
| 5,142,706 A * | 9/1992 | Layhon | 2/424 |
| 5,214,804 A * | 6/1993 | Carey et al. | 2/206 |
| 5,220,689 A * | 6/1993 | Miller | 2/12 |
| D337,645 S * | 7/1993 | Guziejka | D2/884 |
| D355,485 S * | 2/1995 | Hubbard et al. | D24/110.2 |
| 5,546,099 A * | 8/1996 | Quint et al. | 345/8 |
| 5,617,584 A * | 4/1997 | Brennan | 2/206 |
| 5,634,210 A * | 6/1997 | King et al. | 2/9 |
| 5,694,647 A * | 12/1997 | Crickmore | 2/172 |
| 5,950,241 A * | 9/1999 | Gomez | 2/172 |
| 5,950,888 A * | 9/1999 | Nolan-Brown | 224/172 |
| 5,956,760 A * | 9/1999 | Wine et al. | 2/9 |

(Continued)

FOREIGN PATENT DOCUMENTS

JP    2001129014    *  5/2001    ............. A61F 9/004

OTHER PUBLICATIONS

JPO Machine translation of JP2001129014 (May 2001), entire document.*

*Primary Examiner* — Bobby Muromoto, Jr.
(74) *Attorney, Agent, or Firm* — Incorporating Innovation LLC; Charlena Thorpe, Esq.

(57) ABSTRACT

A sleep shield apparatus that can provide privacy, peacefulness, and protection in a public environment such as an airplane, airport, bus, or train is provided.

19 Claims, 5 Drawing Sheets

(56) References Cited

U.S. PATENT DOCUMENTS

| | | | | |
|---|---|---|---|---|
| 6,029,278 | A * | 2/2000 | Lopez | 2/209.13 |
| 6,088,836 | A * | 7/2000 | de Cordova | 2/171 |
| 6,651,256 | B1 * | 11/2003 | Swift | 2/171 |
| 6,718,554 | B1 * | 4/2004 | Langston | 2/49.1 |
| D518,625 | S * | 4/2006 | Barnhouse | D2/866 |
| 7,051,371 | B2 * | 5/2006 | Tobin et al. | 2/9 |
| 7,188,374 | B2 * | 3/2007 | Carey | 2/209.11 |
| 7,343,630 | B2 * | 3/2008 | Lee | 2/175.6 |
| 7,681,251 | B2 * | 3/2010 | Carey | 2/171 |

* cited by examiner

SLEEP SHIELD APPARATUS

BACKGROUND

There has been a trend in the airline industry of increased delays to destinations. Accordingly, travelers often experience long periods of time in the airport. Furthermore, flights to certain destinations (e.g., a non-stop flight to another country such as China) can be very long. Long delays and long trips also are common in other transportation industries such as ground and rail. During long delays or long trips, a traveler may desire to rest including sleep, but oftentimes the traveler cannot find private accommodations. Accordingly, the traveler must attempt to rest in public where the traveler is surrounded by uncomfortable distractions such as lights, noise, and other people.

While resting in public areas, travelers may desire some minimum level of privacy, peacefulness, and protection. For example, some travelers may desire to avoid being viewed while sleeping. In a close environment such as an airplane, bus, or train, a traveler may find it uncomfortable to sleep publicly next to a stranger. A traveler may also want to filter light and/or sound for a more peaceful rest. Still further, some travelers may feel better protected (e.g., from germs) if their orifices, such as their mouths, are shielded while sleeping.

Travelers typically resort to placing a coat (or blanket if available) over their head to cover their face for privacy, peacefulness, and/or protection. However, these items are usually heavy and may easily fall off when the traveler moves even slightly. These items also are not designed to be placed over the head and face. Therefore, when these items are placed over the head, breathing can be difficult due to the lack of airflow and the temperature underneath the items can rise to an uncomfortable level.

Products designed for sleeping, such as eye covers to suppress light to the eyes, are limited because they only cover the eyes and do not provide concealment or protection to other parts of the face or body. For example, U.S. Pat. No. 2,874,385 and U.S. Pat. No. 6,088,836 disclose an eye cover that only covers the eyes.

Products that cover the face typically are designed for active use, for example, for use while skiing or transporting harmful materials. Accordingly, these active-wear face covers do not cover the eyes but instead provide means for the users to see while engaging in an activity. U.S. Pat. Nos. 2,119,439; 2,669,717 4,259,748; 5,617,584 are all illustrative of such active-wear face covers.

For the foregoing reasons, there is a need for a sleeping apparatus that can provide privacy, peacefulness, and protection in a public environment.

SUMMARY

In one embodiment of the present invention, a sleep shield apparatus includes an eye shield portion, at least one strap for securing the eye shield to the face, and a lower portion. In one embodiment, the eye shield portion is constructed of a material that fully blocks light from reaching a user's eyes. The sleep shield may also comprise an eye cover attached to the eye shield portion. In one embodiment, the lower portion is configured to cover a lower portion of the face. In another embodiment, the lower portion is configured to cover a portion of the upper torso. In yet another embodiment, the lower portion is configured to cover the upper torso and the arms similar to a blanket. The lower portion may include a storage unit. In one embodiment, the sleep shield includes a nose opening between the eye shield portion and the lower portion and may include a nose cover and/or a nose bridge.

Both the foregoing general description and the following detailed description are exemplary and explanatory only and are not restrictive of the invention, as claimed.

DETAILED DESCRIPTION

Various embodiments of the present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Figure 1A:
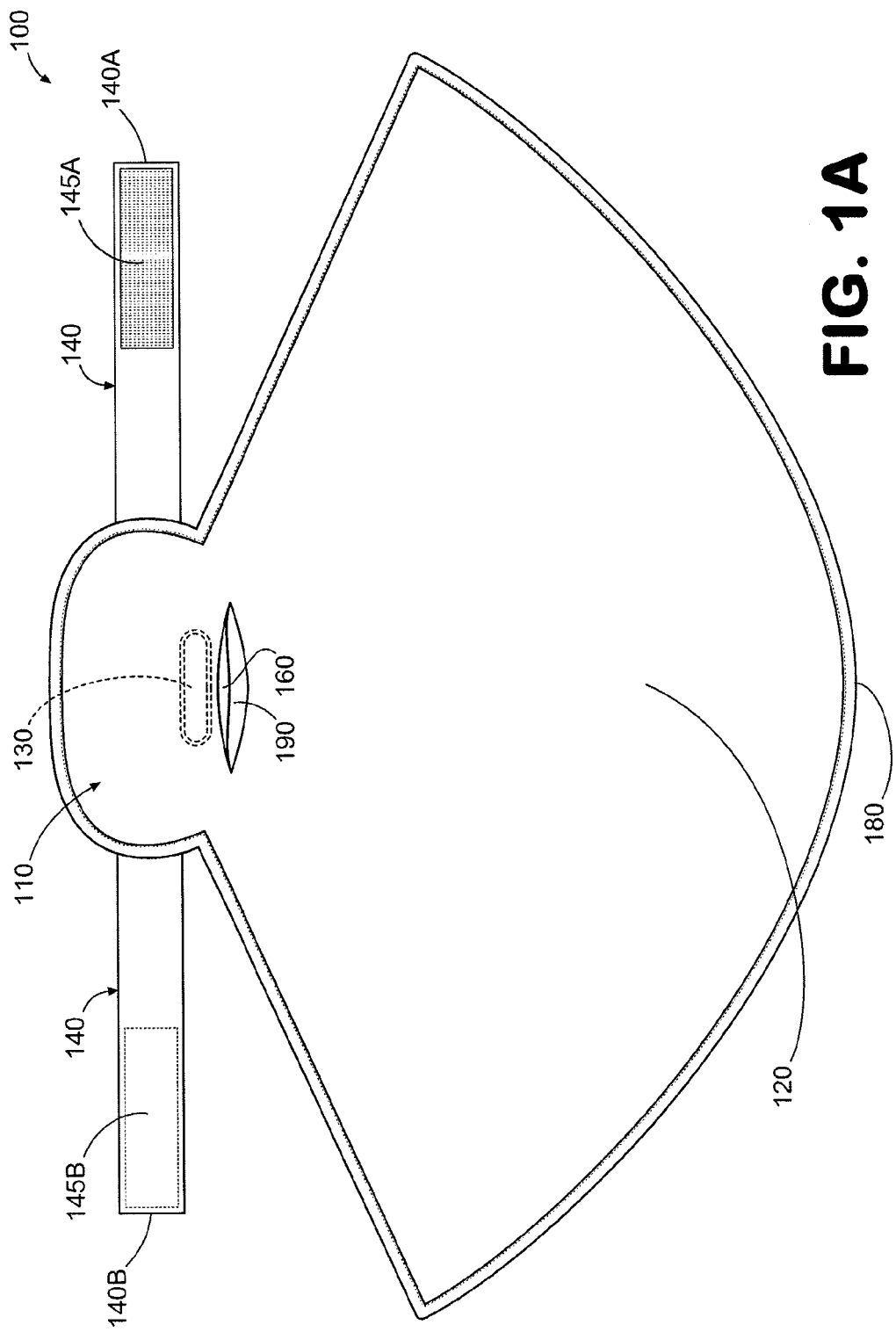
FIG. 1A illustrates a front view of a sleeping apparatus according to one embodiment of the invention.

FIG. 1A illustrates a sleeping apparatus 100 according to one embodiment of the invention. The outer surface (i.e., the surface facing away from the user) and inner surface (i.e., the surface in contact with the user) of the sleeping apparatus 100 may be constructed of any material. However, preferably, the outer surface is constructed of knitted fabrics, woven fabrics, non-woven fabrics, or a similar material. Preferably, the inner surface is constructed of a soft material such as satin, cotton, micro-fiber, soft synthetic, or a soft natural material.

The sleeping apparatus 100 may consist of an eye shield portion 110, lower portion 120, and a head strap 140. The eye shield portion 110 covers the user's eyes. The lower portion 120 may cover the lower portion of the user's face and neck or may extend further down to also cover the user's torso or cover the user similar to a blanket. For example, the lower portion 120 may be proportioned to cover the user's mouth, chin, neck, arms, torso, as well as drape around the sides of the user's face. Although FIG. 1 illustrates one size and shape, the lower portion 120 may be any size (for example as discussed above with respect to the length) or shape. For instance, a lower edge 180 of the lower portion 120 may be curved, straight, or any other shape or design. The head strap 140 secures the eye shield portion 110 to the user's face.

Figure 3:
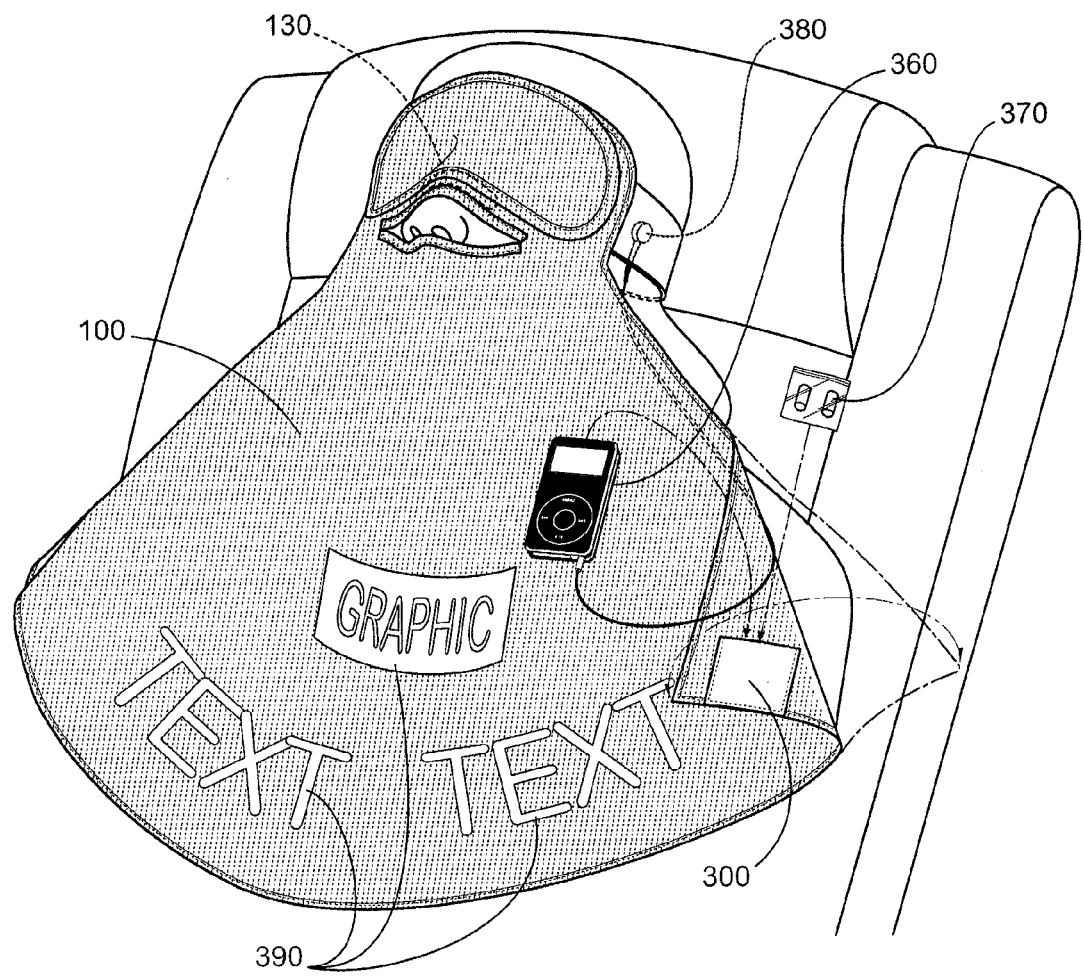
FIG. 3 illustrates an exemplary use of a sleeping apparatus according to one embodiment of the invention.
Figure 4:
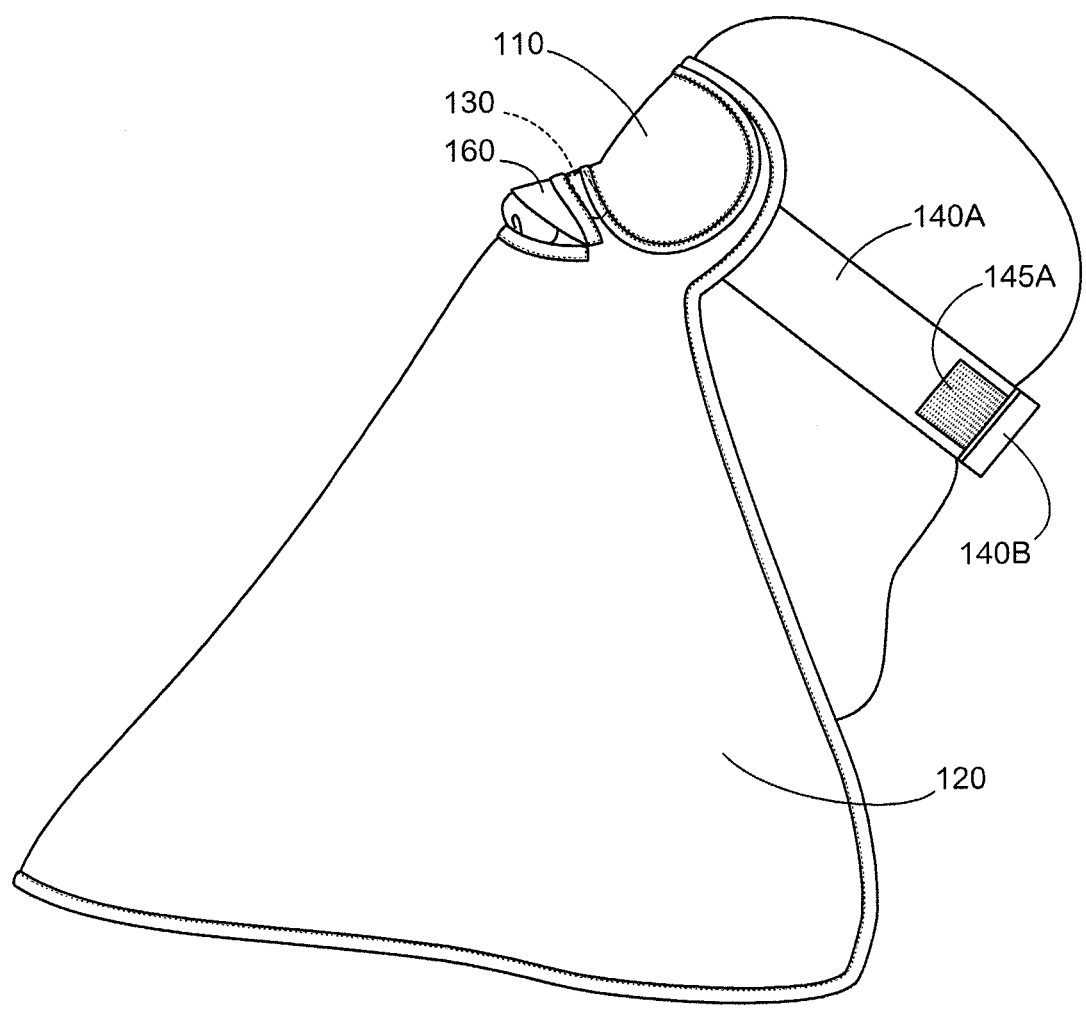
FIG. 4 illustrates a side view of a sleeping apparatus according to one embodiment of the invention.

The sleep shield 100 also may include an opening 190 between the eye shield portion 110 and the lower portion 120. In one embodiment, the width of the opening 190 may be about the length between the nostril and upper lip. The sleep shield 100 may be positioned on the user's head such that the opening 190 is at or near the user's nose to allow the user to breathe more comfortably. The top of the opening 190 may be shaped to fit the contour of the user's nose. As shown in FIGS. 1 and 3, a nose bridge 130 may be added to shape and maintain the nose opening into a comfortable position for the user. The nose bridge 130 may be made from a malleable material such as aluminum or other metal or material. A nose cover 160 may be attached to the sleep shield 100. The nose cover 160 may cover the bridge and bottom of the user's nose. The cover may be made from a silky, smooth material such as satin.

Figure 1B:
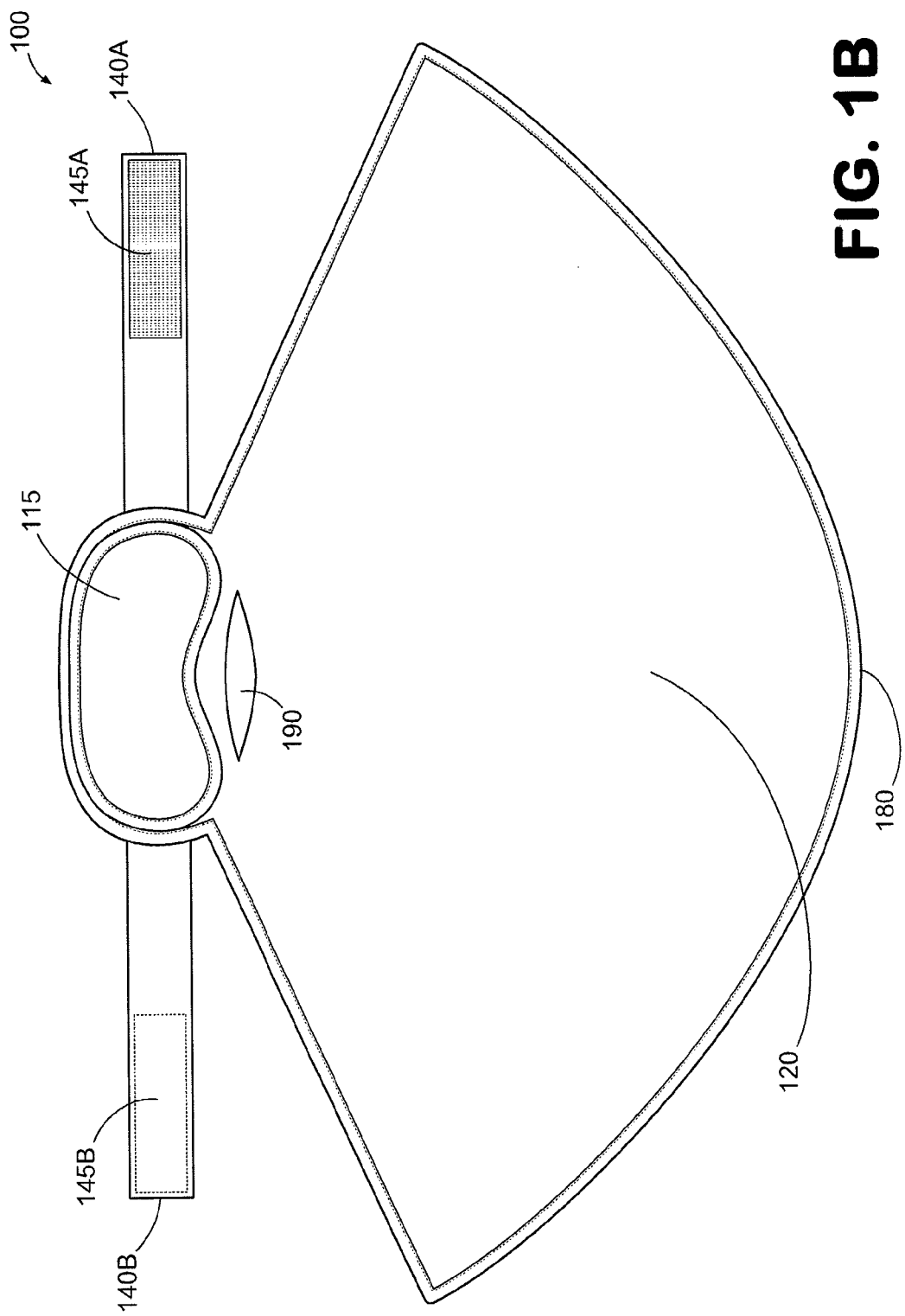
FIG. 1B illustrates a front view of a sleeping apparatus according to another embodiment of the invention.
Figure 2:
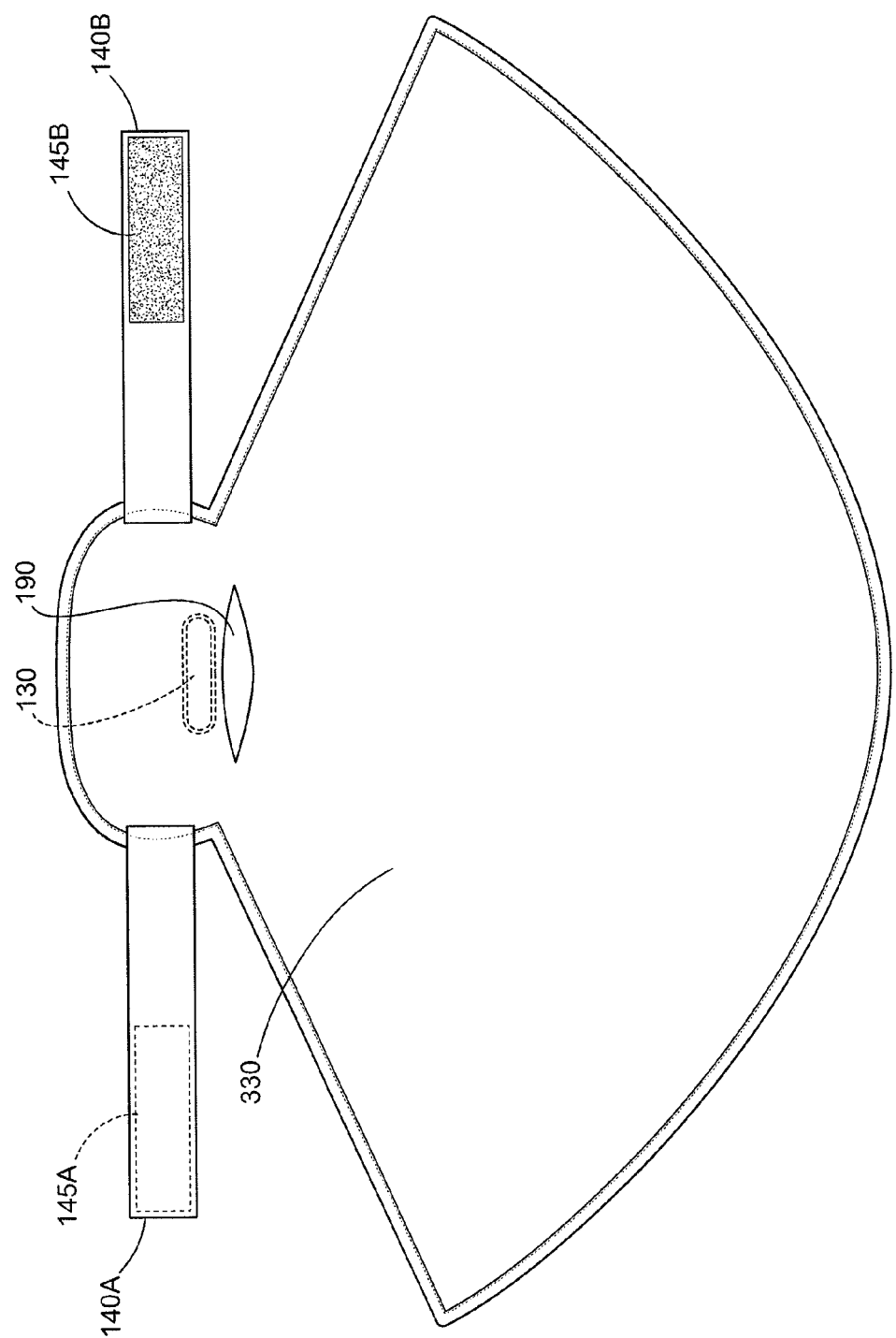
FIG. 2 illustrates a back view of a sleeping apparatus according to one embodiment of the invention.

Typically, the outer surface of the eye shield portion 110 and lower portion 120 are made from the same material. Similarly, the inner surface of the eye shield portion 110 and lower portion 120 are typically made from the same material. However, the sleeping apparatus 100 may be constructed of a number of different materials according to the principles of the inventions. The outer and/or inner surface of the sleeping apparatus 100 may be constructed of a material to prevent light from reaching the user's eyes. As shown in FIG. 1B, depending on the material used for the outer and/or inner surface, it may be desirable to add an additional eye cover 115 on top of the eye shield portion 110 to further block light. The eye cover 115 may be permanently attached or detachable from the sleep shield 100. In one embodiment, the eye shield portion 110 and/or the eye cover 115 may be cupped or convex so that the inner surface of the eye shield portion 110 is at an appropriate distance from the user's eyes to allow for eye movement (e.g., rapid eye movement during sleep).

The head strap 140 may include a first attaching means 145A and a second attaching means 140B that together form any conventional attaching mechanism such as Velcro® or buttons. For instance, the first attaching means 140A may consists of hooks and the second attaching means 140B may consists of loops. Alternatively, the straps 140A, B of the head strap 140 may be used to secure the sleep shield 100 to the user's head by for example tying the straps 140A, B into a knot. The straps 140A, B may be connected to form one continuous strap from one side of the sleep shield 100 to the other side. The head strap 140 may be elastic. In one embodiment of the invention, the head strap 140 may include noise inhibiting ear plugs to be inserted in the user's ears. The ear plugs may be detachable or permanently connected to the head strap 140. The head strap 140 may be detachable from the sleep shield 100.

As illustrated in FIG. 3, the sleeping apparatus 100 may includes a storage unit 300. In one embodiment, the storage unit 300 is located on the inner surface of the lower portion 120. The storage unit 300 may be used to store a broad range of items including, but not limited to, a plane ticket, identification such as a driver's license, ear plugs, or an electronic device such as a portable audio device (such as a mp3 player), a small radio, a cell phone, PDA, or like devices. FIG. 3 illustrates a user storing a portable audio device in storage unit 300 to listen to music while relaxing.

As shown in FIG. 3, the sleep shield 100 may includes text or a graphical design 390. The text or graphical design 390 may be a logo, picture, trademark, or any other graphic or text. The graphic or text may be located anywhere on the sleep shield.

Many modifications and other embodiments of the invention will come to mind to one skilled in the art to which this invention pertains having the benefit of the teachings presented in the forgoing descriptions and the associated drawings. For example, others in the travel industry (e.g., pilots, flight attendants, etc.) that need to rest between shifts may benefit from the sleep shield 100. Still further, the sleep shield 100 may be used by professionals (e.g., doctors) and other employees in a work environment such as an office or designated rest area. The sleep shield 100 also may be used in a private environment such as at home to shield light and noise while resting. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A sleep shield apparatus comprising:
    an eye shield portion comprising a material configured to cover a user's eyes;
    at least one strap for securing the eye shield to the face; and
    a lower portion comprising a material configured to cover a portion of a user's face below a user's eyes wherein the material comprising the eye shield portion and the material comprising the lower portion is configured to form an opening wherein the opening is surrounded on all sides by a portion of the material forming the eye shield portion and the material forming the lower portion and wherein in the opening is configured to provide an opening for a user's nose when the eye shield portion is positioned on the user's eye, further comprising a nosebridge made from a malleable metallic material configured to shape and maintain the nose opening.

2. A sleep shield apparatus of claim 1, wherein the lower portion is configured to cover a lower portion of the face.

3. A sleep shield apparatus of claim 1, wherein the lower portion is configured to cover the mouth.

4. A sleep shield apparatus of claim 1, wherein the lower portion is configured to cover the mouth and chin.

5. A sleep shield apparatus of claim 1, wherein the lower portion is configured to cover the mouth, chin, and at least a portion of the neck area.

6. A sleep shield apparatus of claim 1, wherein the lower portion is configured to extend below the chin.

7. A sleep shield apparatus of claim 1, wherein the lower portion is configured to cover at least a portion of the neck area.

8. A sleep shield apparatus of claim 1, wherein the lower portion is configured to cover a portion of the upper torso.

9. A sleep shield apparatus of claim 1, wherein the lower portion is configured to cover the upper torso and the arms.

10. A sleep shield apparatus of claim 1, wherein the lower portion is configured to cover the upper torso, the arms, and lower body.

11. A sleep shield apparatus of claim 1, wherein the lower portion comprises a storage unit.

12. A sleep shield apparatus of claim 1, wherein the lower portion includes a graphical design.

13. A sleep shield apparatus of claim 1, wherein the eye shield portion is constructed of a material that fully blocks light from reaching a user's eyes.

14. A sleep shield apparatus of claim 1, further comprising an eye cover attached to the eye shield portion.

15. A sleep shield apparatus of claim 14, wherein the lower portion is configured to cover a portion of the upper torso, wherein the lower portion comprises a storage unit, and wherein the lower portion includes a graphical design.

16. A sleep shield apparatus of claim 1, wherein the at least one strap is constructed of an elastic material.

17. A sleep shield apparatus of claim 1, comprising two straps and a fastener to connect the two straps.

18. A sleep shield apparatus of claim 17, herein the fastener comprising hook and loop strips.

19. A sleep shield apparatus of claim 1, further comprising ear covers.

\* \* \* \* \*